(12) United States Patent
Morero et al.

(10) Patent No.: US 11,471,651 B2
(45) Date of Patent: Oct. 18, 2022

(54) BALLOON CATHETER INCLUDING A GUIDEWIRE TUBE WITH A FRICTION-INCREASING OUTER COATING

(71) Applicant: Medtronic, Inc., Minneapolis, MN (US)

(72) Inventors: Massimo Morero, Turin (IT); Chiara Pedroni, Milan (IT)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 16/908,357

(22) Filed: Jun. 22, 2020

(65) Prior Publication Data

US 2021/0393923 A1 Dec. 23, 2021

(51) Int. Cl.
```
A61M 25/06     (2006.01)
A61M 25/00     (2006.01)
A61M 25/10     (2013.01)
```
(52) U.S. Cl.
CPC .... *A61M 25/0662* (2013.01); *A61M 25/0009* (2013.01); *A61M 25/10* (2013.01); *A61M 2025/0681* (2013.01); *A61M 2205/0216* (2013.01); *A61M 2205/0238* (2013.01)

(58) Field of Classification Search
CPC .............. A61M 25/0662; A61M 25/10; A61M 25/0169
See application file for complete search history.

(56) References Cited

U.S. PATENT DOCUMENTS

| | | | |
|---|---|---|---|
| 5,304,134 A | 4/1994 | Kraus et al. | |
| 5,603,991 A | 2/1997 | Kupiecki et al. | |
| 5,833,706 A | 11/1998 | St. Germain et al. | |
| 6,165,166 A * | 12/2000 | Samuelson | B29C 48/12 |
| | | | 604/524 |
| 6,530,938 B1 * | 3/2003 | Lee | A61M 25/0009 |
| | | | 606/191 |
| 6,706,055 B2 * | 3/2004 | Douk | A61M 25/09 |
| | | | 606/200 |

(Continued)

FOREIGN PATENT DOCUMENTS

| | | | |
|---|---|---|---|
| CN | 109701138 A | * | 5/2019 |
| JP | 2000509641 A | * | 8/2000 |

(Continued)

OTHER PUBLICATIONS

Overview of Materials for Silicone Rubber, Matweb Material Property Data, www.matweb.com/search/DataSheet.aspx?MatGUID=cbe7a469897a47eda563816c86a73520&ckck=1 , accessed Nov. 2, 2021 (Matweb, 2021), 4 pp.*

(Continued)

*Primary Examiner* — Jason E Flick
*Assistant Examiner* — Adam J. Cermak
(74) *Attorney, Agent, or Firm* — Shumaker & Sieffert, P.A.

(57) ABSTRACT

In some examples, a catheter (e.g., a balloon catheter) includes a guidewire tube extending through a catheter body and a coating on at least a portion of an outer surface of the guidewire tube. In some examples, the coating is an elastomeric coating. The coating is configured to increase friction between the portion of the outer surface of the guidewire tube and an inner surface of the catheter body when the portion of the outer surface contacts an inner surface of the catheter body.

27 Claims, 6 Drawing Sheets

(56) References Cited

U.S. PATENT DOCUMENTS

| | | | |
|---|---|---|---|
| 7,130,700 B2* | 10/2006 | Gardeski | A61M 25/0021 |
| | | | 607/122 |
| 7,166,100 B2 | 1/2007 | Jordan et al. | |
| 7,628,769 B2 | 12/2009 | Grandt et al. | |
| 7,648,517 B2* | 1/2010 | Makower | A61B 17/12022 |
| | | | 606/169 |
| 8,012,123 B2* | 9/2011 | Wilkins | A61M 25/0045 |
| | | | 604/103 |
| 8,444,608 B2 | 5/2013 | Haslinger et al. | |
| 9,750,625 B2* | 9/2017 | Dorn | A61F 2/95 |
| 9,884,170 B2* | 2/2018 | Campbell | A61M 25/005 |
| 10,905,431 B2* | 2/2021 | Gorochow | A61B 17/12031 |
| 10,993,824 B2* | 5/2021 | Longo | A61F 2/966 |
| 2004/0167439 A1 | 8/2004 | Sharrow | |
| 2005/0080356 A1* | 4/2005 | Dapolito | A61M 25/09 |
| | | | 600/585 |
| 2005/0131450 A1* | 6/2005 | Nicholson | A61B 17/221 |
| | | | 606/200 |
| 2006/0047224 A1* | 3/2006 | Grandfield | A61M 25/09 |
| | | | 600/585 |
| 2006/0184227 A1* | 8/2006 | Rust | A61F 2/07 |
| | | | 623/1.13 |
| 2007/0225746 A1* | 9/2007 | Lee | A61M 25/0045 |
| | | | 606/194 |
| 2013/0085519 A1* | 4/2013 | Kiminami | A61L 29/085 |
| | | | 606/192 |
| 2014/0276407 A1 | 9/2014 | DeVries et al. | |
| 2016/0262883 A1* | 9/2016 | Sandstrom | A61F 2/2436 |
| 2017/0157368 A1* | 6/2017 | Umeda | A61M 25/10 |
| 2017/0304097 A1* | 10/2017 | Corwin | A61F 2/966 |
| 2019/0008667 A1* | 1/2019 | Longo | A61F 2/958 |
| 2019/0240488 A1* | 8/2019 | Tsay | A61B 90/37 |
| 2019/0254699 A1* | 8/2019 | Forde | A61M 16/0497 |
| 2020/0086089 A1* | 3/2020 | Kugler | A61M 25/0012 |
| 2020/0390454 A1* | 12/2020 | Kramer | A61B 17/22 |
| 2021/0022898 A1* | 1/2021 | Kanjickal | A61F 2/07 |

FOREIGN PATENT DOCUMENTS

| | | | | |
|---|---|---|---|---|
| WO | WO-2016035740 A1 * | 3/2016 | | A61M 25/1029 |
| WO | WO-2018092354 A1 * | 5/2018 | | A61M 25/10 |
| WO | WO-2018174243 A1 * | 9/2018 | | A61M 29/00 |

OTHER PUBLICATIONS

Overview of materials for Ethylene Acryslic Acid, 2 pp., https://www.matweb.com/search/datasheet_PDF.aspx?MatGUID=84ec0f699edf443490d9ad0328f36441 (accessed Mar. 21, 2022).*

Hytrel 7246 data sheet, https://dupont.materialdatacenter.com/GB/products/pdf/SI/Hytrel%C2%AE%207246-gb.pdf (Dupont, 2022), 18 pp.*

Primacor data sheet, https://www.matweb.com/search/datasheet_PDF.aspx?MatGUID=e233ee0dcf794744b504713961f89329, (accessed Mar. 21, 2022), 1 pg.*

Extended Search Report from counterpart European Application No. 21180517.1 dated Nov. 25, 2021, 10 pp.

* cited by examiner

BALLOON CATHETER INCLUDING A GUIDEWIRE TUBE WITH A FRICTION-INCREASING OUTER COATING

TECHNICAL FIELD

This disclosure relates to a medical catheter.

BACKGROUND

Catheters may be used in intravascular procedures or other procedures to facilitate minimally invasive access to a target site. For example, an angioplasty catheter may include one or more balloons mounted to the catheter that may be advanced to the target site and inflated to clear or compress a blockage, for example a stenosis. As another example, a stent delivery catheter may include a stent positioned over a balloon, which may be inflated to deploy the stent. A catheter must be flexible enough to navigate tortuous vasculature but be stiff enough to push over long distances. However, balancing these two characteristics may be difficult, resulting in a catheter that is too stiff to curve around very tortuous vessels or too flexible to give good pushability over long distances or through complex lesions.

SUMMARY

This disclosure describes example catheters (e.g., balloon catheters) that include a guidewire tube extending through a catheter body and a coating on at least a portion of an outer surface of the guidewire tube. The coating is configured to increase friction between the portion of the outer surface of the guidewire tube and an inner surface of the catheter body when the portion of the outer surface contacts the inner surface of the catheter body. The increased friction between the guidewire tube and the catheter body may improve the pushability of the catheter by at least increasing a stiffness of the catheter when the portion of the guidewire tube contacts the inner surface of the catheter body. For example, due at least in part to the coating on the guidewire tube, the guidewire tube and the catheter body mechanically couples together at the location where the guidewire tube contacts the inner surface of the catheter body, which may increase a stiffness of the catheter relative to examples in which the guidewire tube does not mechanically couple to the catheter body.

In some examples, the coating comprises an elastomeric coating. In addition, in some examples, the coating is applied over the entire outer surface of the guidewire tube. In other examples, the coating is applied to only part of the outer surface of the guidewire tube. For example, the coating may be applied to the outer surface of the guidewire tube in a predetermined pattern, e.g., longitudinal stripes, a helical pattern, lateral stripes, or the like, and/or over at least part of the outer surface of the guidewire tube extending through a lumen of the catheter body and not over the outer surface of the guidewire tube longitudinally aligned with a balloon of the catheter. In any of these examples, the coating is separate from the guidewire tube, e.g., is not co-extruded with the guidewire tube and is not a structural layer of the guidewire tube. In some examples, the coating has a lower hardness than the materials used to form the guidewire tube, such that the coating would be unsuitable for defining the structure of the guidewire tube.

The details of one or more aspects of the disclosure are set forth in the accompanying drawings and the description below. Other features, objects, and advantages of the systems and techniques described in this disclosure will be apparent from the description and drawings, and from the claims.

DETAIL DESCRIPTION

In examples described herein, a catheter includes an elongated catheter body, a guidewire tube extending through a lumen of the catheter body, and, in some examples, a balloon. An inner surface of the catheter body ("catheter body inner surface") defines the lumen through which the guidewire tube extends. In some examples, the guidewire tube extends through the balloon. The balloon catheter further comprises a coating on at least a portion of an outer surface ("guidewire tube outer surface") of the guidewire tube, where the coating is configured to increase friction (e.g., kinetic friction and/or static friction) between the portion of the guidewire tube outer surface and the catheter body inner surface when the portion of the guidewire tube outer surface contacts the catheter body inner surface. That is, when at least a portion of the guidewire tube outer surface contacts the catheter body inner surface, for a given force applied to the catheter in a direction generally parallel to a longitudinal axis of the catheter, the coating enables at least that portion of the guidewire tube outer surface to move less relative to the catheter body inner surface relative to examples in which the portion of the guidewire tube outer surface does not include the coating.

The increased friction between the portion of the guidewire tube outer surface and the catheter body inner surface may increase the pushability of the catheter by enabling the guidewire tube and the catheter body to mechanically couple together at the location where the guidewire tube contacts the catheter body inner surface. At least a portion of the guidewire tube outer surface may, for example, contact the catheter body inner surface when the catheter body is curved (e.g., positioned in a curved blood vessel). The mechanical coupling between the guidewire tube and the catheter body may increase a stiffness of the catheter, relative to examples in which the guidewire tube does not frictionally engage with the catheter body and instead slides relative to the catheter body inner surface. The increased stiffness of the catheter will enable the catheter to better transmit a pushing force from a proximal portion of the catheter to a distal portion of the catheter.

The coating can comprise any suitable material that exhibits a relatively high friction relative to the catheter body inner surface. In some examples, the coating comprises an elastomeric coating and/or a polymer coating. In other examples, however, the coating can include a polymer, such as a relatively soft polymer (e.g., having a hardness of 20 Shore A or less), that does not have elastomeric properties. The soft polymer can, for example, have a hardness that is at least three times lower than the hardness of the guidewire tube, which can be the overall hardness of the guidewire tube in examples in which the guidewire tube has a multi-layer construction or a hardness of one specific layer of a multilayer guidewire tube. In any of these examples, the coating can be hydrophobic. Thus, an outermost surface of guidewire tube can be hydrophobic in regions where the coating is applied. An example elastomeric, hydrophobic polymer that may be used to form the coating includes elastomers manufactured by Kraton Corporation of Houston, Tex.

For ease of description, the coating is primarily referred to as an elastomeric coating herein, but the description herein may also apply to a polymer coating, which may or may not be elastomeric. An elastomeric coating may be characterized by its visco-elastic behavior (including both elasticity and viscosity) due to the weakness of the inter-molecular bonds and, in some cases, may also be characterized by its toughness.

In some examples, the coating is applied over the entire outer surface of the guidewire tube, i.e., on the outer surface along an entire length of the guidewire tube. In other examples, the coating is applied over less than the entire outer surface of the guidewire tube. For example, the coating may be applied to the outer surface of the guidewire tube in a predetermined pattern, e.g., longitudinal stripes, a helical pattern, lateral stripes, or the like or combinations thereof. The predetermined pattern can provide the guidewire tube with the desired friction properties while reducing the quantity of coating required to manufacture the catheter. In addition to or instead of the predetermined pattern, in some examples, the coating is present on only a part of a length of the guidewire tube, such as only the part of the guidewire tube outer surface extending through a lumen of the catheter body; in this example, the coating is not positioned over a section of the guidewire tube outer surface longitudinally aligned with a balloon of the catheter. As discussed above, in some examples, the guidewire tube extends through the balloon. Presence of the coating over the portion of the guidewire tube longitudinally aligned with the balloon, and, therefore, extending through the balloon, may adversely impact some properties of the balloon, such as the balloon crossing profile and deflation time. Accordingly, it may be desirable in some examples to minimize or even eliminate the coating present within the volume of the balloon.

In any of the examples described above, the coating is separate from the guidewire tube, e.g., is not co-extruded with the guidewire tube and is not a structural layer of the guidewire tube.

The guidewire tube has any suitable structure that is configured to receive a guidewire. In some examples, the guidewire tube has a monolayer structure, while in other examples, the guidewire tube has a multilayer structure (e.g., two layers, three layers, or four or more layers). For example, the guidewire tube can include two or more co-extruded layers. In some examples in which the guidewire tube has a multilayer structure, the elastomeric coating on an outermost surface of the guidewire tube is separate from and applied to an outermost surface of the multilayer guidewire tube. That is, the elastomeric coating does not form one of the layers of the guidewire tube. In some examples, the elastomeric coating may have a lower hardness than the materials used to form the guidewire tube, such that the coating would be unsuitable for defining the structure of the guidewire tube and/or would not be suitable for co-extruding with the other materials of the multilayer guidewire tube to form the guidewire tube. For example, the elastomeric coating may have a melting temperature different from the materials used to form the guidewire tube, such that it would not be suitable for being co-extruded with the guidewire tube.

The catheters described herein may be formed using any suitable technique. In example techniques, the guidewire tube is first formed (e.g., extruded) and then the elastomeric coating is applied to the guidewire tube outer surface, e.g., along the entire outermost surface or only along part of the outermost surface. In some examples, the coating is applied to the guidewire tube by dip coating, spray coating, or brushing the coating onto the guidewire tube.

In some examples, a distal portion (e.g., a distal end) of the balloon is connected to the guidewire tube. In some examples, both the distal end and the proximal end of the balloon are connected to the guidewire tube, while in other examples, the proximal end of the balloon is connected to the catheter body or another structure.

The example catheters described herein may be used for any suitable medical procedure, such as, but not limited to, procedures to treat defects in the neurovasculature, peripheral vasculature, and coronary vasculature. Example defects include, but are not limited to, vessel occlusions.

Figure 1A:
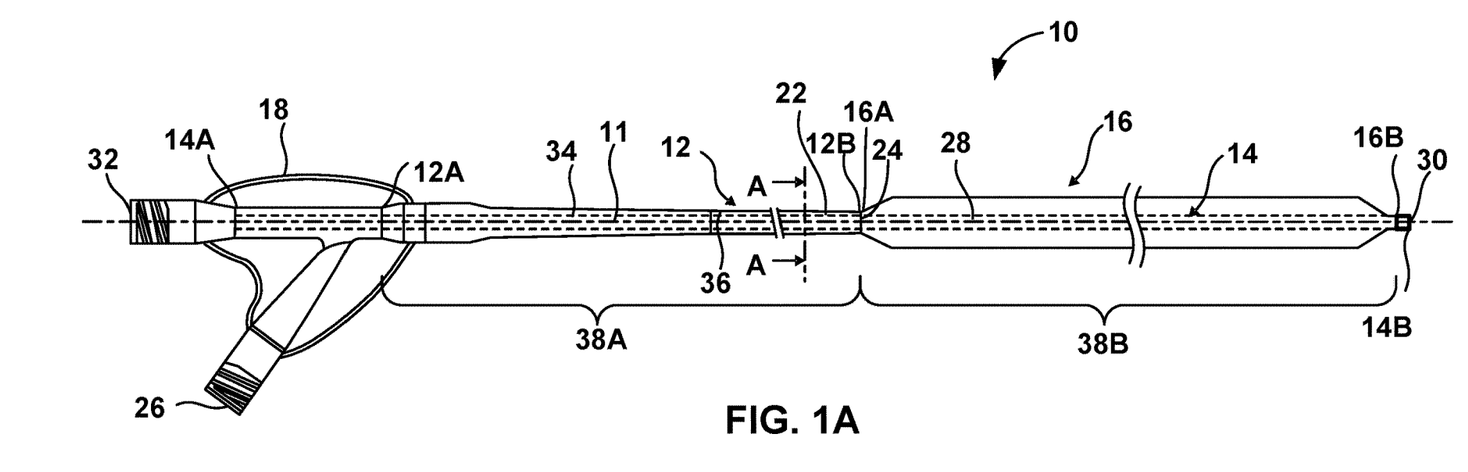
FIG. 1A is a side elevation view of an example catheter that includes a guidewire tube and a coating on at least a portion of the guidewire tube.
Figure 1B:
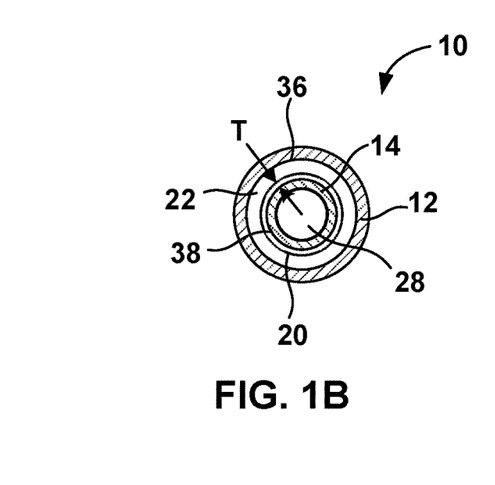
FIG. 1B is a cross-sectional view of the catheter of FIG. 1A, where the cross-section is taken along line A-A in FIG. 1A in a direction orthogonal to a central longitudinal axis of the catheter.

FIG. 1A is a side elevation view of an example catheter 10 and FIG. 1B is a cross-sectional view of the catheter 10, where the cross-section is taken along line A-A in FIG. 1A in a direction orthogonal to a central longitudinal axis 11 of the catheter 10. The catheter 10 includes a catheter body 12, which is an outer elongated member, a guidewire tube 14, which is an inner elongated member, a balloon 16, a hub 18, and a coating 20 on an outer surface of the guidewire tube 14. As discussed in further detail below, the coating 20 is configured to increase friction (e.g., kinetic friction and/or static friction) between the guidewire tube 14 and an inner surface of the catheter body 12 when the guidewire tube 14 contacts the inner surface of the catheter body. For example, a first coefficient of kinetic friction between the coating 20 and the inner surface of the catheter body 12 may be higher than a second coefficient of kinetic friction between the material forming an outermost surface of the guidewire tube 14 and the inner surface of the catheter body 12.

The catheter body 12 is an elongated structure (e.g., a tube) that extends along the longitudinal axis 11 from a proximal end 12A to a distal end 12B and defines at least one inner lumen 22 (e.g., one inner lumen, two inner lumens, or three inner lumens). At least one of the inner lumens 22 terminates at a distal opening 24 at the distalmost end 12B of the catheter body 12. In the example shown in FIG. 1A, the proximal end 12A of the catheter body 12 is received within a hub 18 and is mechanically connected to the hub 18 via an adhesive, welding, or another suitable technique or combination of techniques. An entry port 26 defined by the hub 18 is aligned with the inner lumen 22 ("catheter body lumen") of the catheter body 12, such that the inner lumen 22 may be accessed via the entry port 26.

The catheter body 12 may be formed from any suitable material. For example, the catheter body 12 may be formed from a metal, a polymer, or combinations thereof.

The catheter 10, including the catheter body 12 and the guidewire tube 14, may have any suitable dimensions, which may depend upon the medical procedure with which the catheter 10 is intended to be used. For example, the catheter 10 can have an overall length of about 80 centimeters (cm) to about 200 cm. The catheter body 12 can have any suitable length measured from the proximal end 12A to the distal end 12B, such as, but not limited to, about 50 cm to about 170 cm, such as about 75 cm, about 90 cm, or about 135 cm (e.g., exactly these lengths or approximately these lengths to the extent permitted by manufacturing tolerances). The catheter body 12 may have any suitable maximum dimension (e.g., a diameter) in cross-section, the cross-section being taken in a direction orthogonal to the longitudinal axis 11. The guidewire tube 14 can have any suitable length and any suitable maximum dimension (e.g., a diameter) in cross-section, and is longer than the catheter body 12 and has a greater diameter than the catheter body 12 in some examples. For example, the guidewire tube 14 can have a length from the proximal end 14A to the distal end 14B of about 80 cm to about 200 cm. In some examples, the guidewire tube 14 has a diameter of about 0.40 millimeters (mm) to about 0.9 mm.

In some examples, an outer diameter of the catheter body 12 may be about 2 French to about 12 French, such as about 3 French or about 6 French. The measurement term French, abbreviated Fr or F, is three times the diameter of a device as measured in mm. Thus, a 6 French diameter is about 2 mm (e.g., about 1.8 mm), a 5 French diameter is about 1.67 mm, a 4 French diameter is about 1.33 mm, and a 3 French diameter is about 1 mm. The term "about" or "approximately" as used herein with dimensions may refer to the exact value of the dimension, such as when used to describe numerical values, or a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, the catheter body 12 and/or the guidewire tube 14 may include one or more radiopaque markers, which may help a clinician determine the positioning of the catheter 10 relative to a target treatment site. For example, one or more radiopaque markers may be positioned proximal to the balloon 16, distal to the balloon 16, at or just proximal to a distal end 12B of the catheter body 12, at or just proximal to a distal end 14B of the guidewire tube 14, or combinations thereof.

The guidewire tube 14 is an elongated structure (e.g., a tube) that extends along the longitudinal axis 11 from a proximal end 14A to the distal end 14B and defines at least one inner lumen 28 ("guidewire tube lumen") that terminates at a distal opening 30 at the distalmost end 14B of the guidewire tube 14. The lumen 28 can be configured to receive a medical device, such as a guidewire or a catheter, and/or a fluid to be delivered to a target site within a patient, such as a contrast agent and/or a therapeutic agent. Thus, guidewire tube 14 can be any suitable structure and is not limited to structures configured to receive guidewires.

In the example shown in FIG. 1A, the proximal end 14A of the guidewire tube 14 is received within the hub 18 and is mechanically connected to the hub 18 via an adhesive, welding, or another suitable technique or combination of techniques. An entry port 32 defined by the hub 18 is aligned with the guidewire tube lumen 28, such that the guidewire tube lumen 28 may be accessed via the entry port 32.

The guidewire tube 14 extends at least partially through the catheter body lumen 22 and extends distally past the distal end 12B of the catheter body 12. That is, a distal end 14B of the guidewire tube 14 is distal to a distal end 12B of the catheter body 12. In some examples, the catheter body 12 and the guidewire tube 14 are coaxial, while in other examples, the guidewire tube 14 can be offset relative to central longitudinal axis 11 of catheter 10.

The catheter body 12 and the guidewire tube 14 may be formed from any suitable material. For example, the catheter body 12 and the guidewire tube 14 may be formed from a metal, a polymer, or combinations thereof. The catheter body 12 and the guidewire tube 14 can have a monolayer structure or a multilayer structure (e.g., two layers, three layers, or four or more layers). For example, the guidewire tube 14 can include two, three, or more co-extruded layers. In some examples in which the guidewire tube 14 is a multilayer tube, an innermost layer of the guidewire tube 14 can be selected to be relatively lubricious (e.g., high-density polyethylene (HDPE)), an outermost layer can be selected to have a higher durometer than the innermost layer to provide increased resistance to collapse and enhanced pushability, and a middle layer can be used to bond the innermost and outermost layers together.

Figure 2:
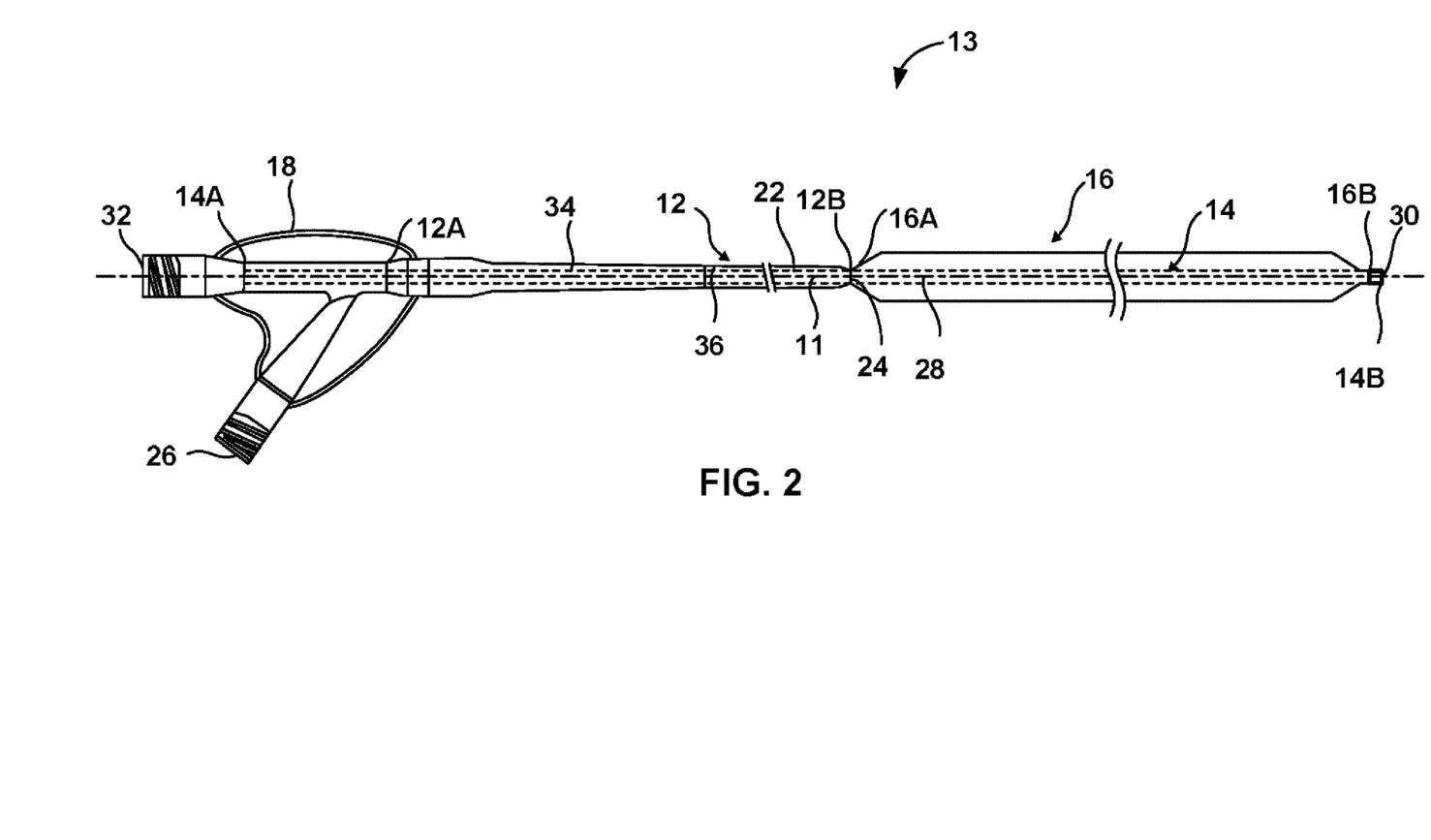
FIG. 2 is side elevation view of an example catheter that includes a guidewire tube and a coating on at least a portion of the guidewire tube.

The balloon 16 is mechanically connected directly or indirectly (e.g., with a tie layer that facilitates adhesion) to the guidewire tube 14 and, in some examples, to the catheter body 12. For example, as shown in FIG. 1A, a proximal end 16A of the balloon 16 is mechanically connected (e.g., welded, adhered, or otherwise secured) to the distal end 12B of the catheter body 12 and a distal end 16B of the balloon 16 is mechanically connected (e.g., welded, adhered, or otherwise secured) to the guidewire tube 14 (e.g., the distal end 14B of the guidewire tube 14 or a location more proximal to the distal end 14B). In other examples, as shown in FIG. 2 with respect to an example catheter 13, the proximal end 16A of the balloon 16 can be mechanically connected to the guidewire tube 14. The configuration of the guidewire tube 14 described herein, which includes a coating 20 on at least a portion of an outer surface of the guidewire tube 14, can be used with any suitable balloon arrangement, as well as with catheters that do not include a balloon.

The balloon 16 is configured to expand from a collapsed configuration to an expanded configuration via an inflation fluid delivered to the balloon 16 via the catheter body lumen 22. The balloon 16 may be inflated to any suitable pressure via an inflation fluid (e.g., saline) delivered to the balloon 16 via an inflation lumen of catheter body 12. In the example shown in FIGS. 1 and 2, the catheter body lumen 22 functions as an inflation lumen, e.g., an inflation fluid can flow to the balloon 16 through a radial space between an inner surface 36 of the catheter body 12 defining the catheter body lumen 22 and an outermost surface 38 of the guidewire tube 14. For example, as shown in FIG. 1A, an inflation fluid (e.g., saline) can be introduced into the balloon 16 via the entry port 26 and the catheter body lumen 22, which are all in fluid communication with each other.

The balloon 16 can be configured (e.g., sized and shaped) for any suitable medical procedure. For example, the balloon 16 can be configured to be inflated to clear or compress a blockage (e.g., a stenosis) in vasculature of a patient. In other examples, a medical device, such as a stent, may be positioned on an outer surface of the balloon 16 and the balloon 16 can be inflated in order to deploy the medical device at a target site within vasculature of a patient. The balloon 16 can have any suitable length. In some examples, the balloon 16 has a length of about 12 mm to about 300 mm. In some examples, a distal-most end of the balloon 16 is separated from the distal end 14B of the guidewire tube 14 by a distance of about 0.25 cm to about 1.5 cm, although other balloon positions can be used in other examples.

The balloon 16 may be formed from any suitable material, such as, but not limited to, polyamides, for example, nylons, polyamide 6 (PA 6), or polyamide 66 (PA 66), polycarbonates (PC), polyethylenes (for example, high density polyethylenes (HDPE) or low density polyethylenes (LDPE)), polyethylene terephthalate (PET), thermoplastic elastomers (TPE) (for example, polyether block amides (PEBAs)), copolymers, or coextrusions thereof. In some examples, the balloon 16 may be made of an expandable material (e.g., made of a stretchable material that expands under pressure).

The hub 18 is positioned at the proximal end of the catheter 10 and defines entry ports 26, 32 through which the catheter body lumen 22 and the guidewire lumen 28, respectively, may be accessed and, in some examples, closed. For example, the hub 18 may include a luer connector for connecting to another device, a hemostasis valve, or another mechanism or combination of mechanisms. In some examples, the catheter 10 includes a strain relief member 34, which may be a part of the hub 18 or may be separate from the hub 18. In other examples, the proximal end of the catheter 10 can include another structure in addition to, or instead of, the hub 18.

Although FIGS. 1A and 2 illustrate a particular arrangement of the catheter body proximal end 12A and the guidewire tube proximal end 14A relative to the hub 18, in other examples, the catheter body proximal end 12A and/or the guidewire tube proximal end 14A can have another position relative to the hub 18. For example, the catheter body proximal end 12A may be positioned more distally or proximally than the location shown in FIG. 2. In addition, in some examples, the catheter 10 may not include a balloon 16 or may include more than one balloon.

The guidewire tube 14 extends through the catheter body lumen 22 and, in some cases, is not directly attached to the catheter body 12. While in some examples, the guidewire tube 14 has a fixed longitudinal position relative to the catheter body 12, e.g., due at least in part to the way the catheter body 12, the guidewire tube 14, the balloon 16, and the hub 18 are connected to each other, the guidewire tube 14 may still move relative to catheter body 12 in a direction transverse to the longitudinal axis 11. That is, the section of the guidewire tube 14 extending through the catheter body lumen 22 may not have a fixed lateral (or radial) position relative to an inner surface 36 (FIG. 1B) of the catheter body 12 defining the catheter body lumen 22. As a result, in some situations, such as when at least a part of the catheter 10 assumes a curved shape as the catheter 10 is being navigated through vasculature of a patient to a target site, at least some portions of the outer surface 38 (FIG. 1B) of the guidewire tube 14 may contact the inner surface 36 of the catheter body 12 ("catheter body inner surface").

Figure 3:
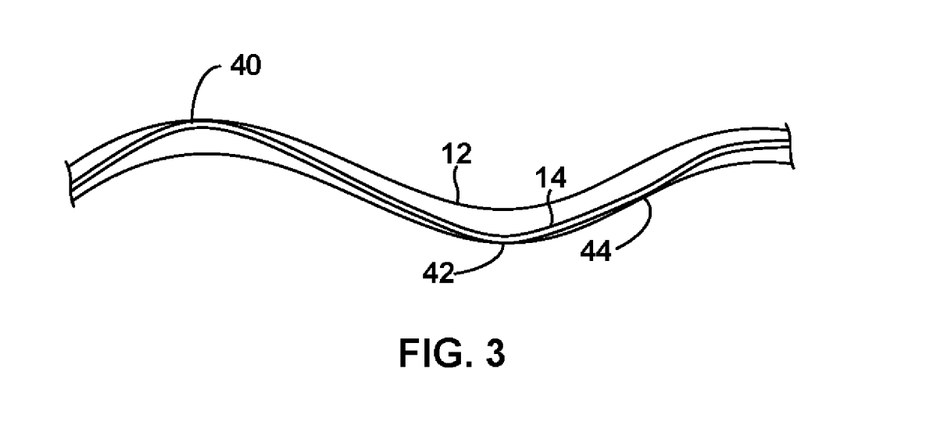
FIG. 3 is a conceptual cross-sectional side view of part of the catheter of FIGS. 1A-2 when it is curved and illustrates the guidewire tube contacting an inner surface of a catheter body.

FIG. 3 is a conceptual cross-sectional side view of part of the catheter 10 and illustrates a part of the catheter 10 when it is curved and further illustrates the guidewire tube 14 extending through the catheter body lumen 22 and contacting the catheter body inner surface 36. In particular, in the particular configuration shown in FIG. 3, the outer surface 38 of the guidewire tube 14 ("guidewire tube outer surface") contacts catheter body inner surface 36 at locations 40, 42 and 44. When the section of the catheter 10 shown in FIG. 3 is in a straight configuration, such that the catheter body 12 and the guidewire tube 14 are straight, the guidewire tube 14 may not contact the catheter body inner surface 36, e.g., because the guidewire tube 14 is centered within the catheter body lumen 22. However, because the guidewire tube 14 may move in a direction transverse to the longitudinal axis 11 (FIG. 1A) relative to the catheter body 12, when the catheter 10 is curved, the guidewire tube outer surface 38 may come into contact with the catheter body inner surface 36, an example of which is shown in FIG. 3.

The coating 20 on at least a portion of the guidewire tube outer surface 38 may help increase a friction between the portion of the guidewire tube outer surface 38 including the coating 20 and the catheter body 12 relative to examples in which the guidewire tube outer surface 38 does not include the coating 20 and, e.g., directly contacts the catheter body inner surface 36. For example, the coating 20 may be configured such that a first coefficient of kinetic friction between the coating 20 and the catheter body inner surface 36 is higher than a second coefficient of kinetic friction between the guidewire tube outer surface 38 and the catheter body inner surface 36. As a result, more force (e.g., applied along the longitudinal axis 11) is necessary to slide the coating 20 against and relative to the catheter body inner surface 36 than to slide the guidewire tube 14 against and relative to the catheter body inner surface 36.

In some examples, the coating 20 may be referred to as a "sticky" coating because it helps enable the guidewire tube 14 to stick to the catheter body inner surface 36. For a given force applied generally along longitudinal axis 11 and when at least a portion of the guidewire tube outer surface 38 contacts the catheter body inner surface 36, the coating 20 enables at least that portion of the guidewire tube outer surface 38 to move less relative to the catheter body inner surface 36 relative to examples in which the portion of the guidewire tube outer surface 38 does not include the coating 20.

The increased friction between the one or more portions of the guidewire tube outer surface 38 and the catheter body inner surface 36 increases the pushability of the catheter 10, which may enhance the trackability of catheter 10 through tortuous vasculature. Increased pushability may, for example, be characterized by better transmission of a pushing force from a proximal portion of the catheter 10 to a distal portion of the catheter 10. For example, the coating 20 may enable the guidewire tube 14 and the catheter body 12 to mechanically couple together at the locations 40, 42 where the coating 20 contacts the catheter body inner surface 36. The mechanical coupling between the guidewire tube 14 and the catheter body 12 increases a stiffness and column strength of the catheter 10, relative to examples in which the guidewire tube 14 slides more relative to the catheter body inner surface 36. In the example shown in FIG. 3, the catheter 10 may have a higher column strength due to the mechanical coupling at the locations 40, 42 between the guidewire tube 14 and the catheter body 12 facilitated by the coating 20.

The coating 20 can comprise any suitable material that exhibits a relatively high friction relative to the catheter body inner surface 36. In some examples, the coating comprises an elastomeric coating and/or a polymer coating, such, but not limited to, as a hydrophobic and elastomeric polymer. In other examples, however, the coating can include a polymer, such as a relatively soft polymer (e.g., having a hardness of 20 Shore A or less), that does not have elastomeric properties. The coating 20 can, for example, have a hardness that is at least three times lower than the hardness of the guidewire tube 14, which can be the overall hardness of the guidewire tube 14 in examples in which the guidewire tube has a multilayer construction or a hardness of one specific layer of a multilayer guidewire tube 14. In any of these examples, the coating can be hydrophobic. Thus, in some examples, the one or more portions of the guidewire tube outer surface 38 having the coating 20 are hydrophobic due to the properties of the coating.

The coating 20 is separate from the guidewire tube 14 and is coated on the guidewire tube outer surface 38. That is, the coating 20 does not form one of the extruded layers of the guidewire tube 14. In some examples, the coating 20 may have a lower hardness and/or a different melting temperature than the materials used to form the guidewire tube 14, such that the coating 20 would be unsuitable for defining the structure of the guidewire tube 14 and/or would not be suitable for co-extruding with the other materials of the guidewire tube 14 to form the guidewire tube 14.

The coating 20 can have any suitable thickness T (FIG. 1B), which is measured in a direction orthogonal to the longitudinal axis 11. In some examples, the coating 20 has a thickness of about 0.001 mm to about 0.1 mm. In some of these examples, the guidewire tube 14 has a diameter of about 0.4 mm to about 0.9 mm.

The coating 20 can be applied to the guidewire tube outer surface 38 using any suitable technique, such as, but not limited to, dip coating, spray coating, or brushing the material defining the coating 20 over the guidewire tube outer surface 38.

In some examples, the coating 20 is applied over the entire guidewire tube outer surface 38. In other examples, the coating 20 is applied over only part of the entire guidewire tube outer surface 38, such that some portions of the outer surface 38 are devoid of the coating 20. For example, the coating 20 may be applied over all or part of the guidewire tube outer surface 38 extending through the catheter body lumen 22 (shown as longitudinal section 38A in FIG. 1A) and is not positioned over a longitudinal section 38B of the guidewire tube outer surface 38 longitudinally aligned with the balloon 16. In addition to or instead of this arrangement of the coating 20, the coating 20 may not be over a proximal portion of the guidewire tube 14 that is intended to remain outside a patient during a medical procedure. As other examples, the coating 20 may be applied to the outer surface of the guidewire tube in a predetermined pattern, e.g., longitudinal stripes, a helical pattern, lateral stripes, or the like. The predetermined pattern can provide the guidewire tube with the desired friction properties while reducing the quantity of coating required to form the catheter.

Figure 4:
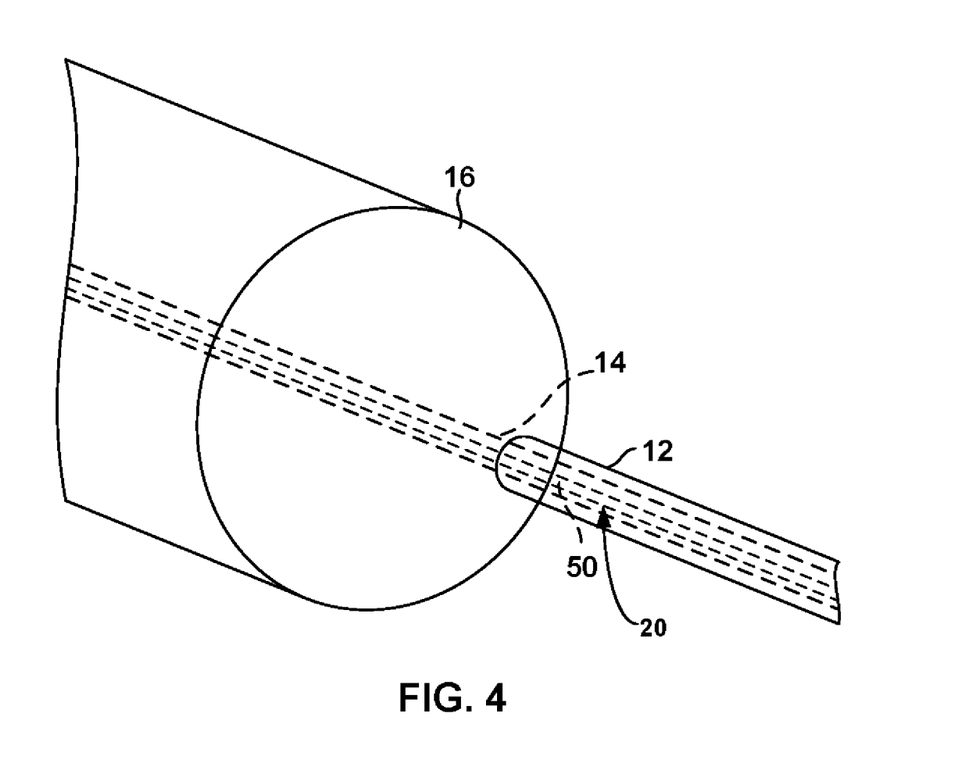
FIG. 4 is a perspective view of an example of a guidewire tube and a coating applied to an outer surface of the guidewire tube in longitudinal stripes.

FIGS. 4-8 illustrate examples of predetermined patterns of the coating 20. FIG. 4 illustrates a perspective view of an example of the guidewire tube 14 and coating 20 in which the coating 20 is applied to the guidewire tube outer surface 38 in one or more longitudinal stripes 50 extending along the longitudinal axis 11 of the catheter 10. A plurality of longitudinal stripes 50 are shown in FIG. 4. In some examples, the longitudinal stripes 50 are substantially parallel to the longitudinal axis 11 (e.g., parallel or nearly parallel to the extent permitted by manufacturing tolerances). The longitudinal stripes 50 can have any suitable length (the length being measured along the longitudinal axis 11) and width (e.g., measured in a circumferential direction in examples in which the guidewire tube 14 has a circular cross-section, the cross-section being taken in a direction orthogonal to the longitudinal axis 11, or in an analogous direction in examples in which the guidewire tube 14 does not have a circular cross-section). For ease of description, the guidewire tube 14 is primarily referred to herein as having a circular cross-section, but the guidewire tube 14 can have other cross-sectional shapes in other examples.

In some examples, the longitudinal stripes 50 extend from the proximal end 14A to the distal end 14B of the guidewire tube 14, while in other examples, the longitudinal stripes 50 extend only partially along a length of the guidewire tube 14. For example, in some examples, the longitudinal stripes 50 are not on a section of the guidewire tube outer surface 38 that extends past a distal end 12B of the catheter body 12 and/or the section of the guidewire tube outer surface 38 that overlaps with the balloon 16.

The width of the longitudinal stripes 50 and the distance between adjacent longitudinal stripes 50 may be selected to increase the possibility of the coating 20, rather than the guidewire tube outer surface 38, directly contacting the catheter body inner surface 36 when the catheter 10 is curved or otherwise bent. In some examples, each longitudinal stripe 50 subtends about 5% to about 40% of the outer perimeter of the guidewire tube 14, such as about 5% to about 35%, or about 10% to about 20%. The longitudinal stripes 50 can be separated from an adjacent longitudinal stripe 50 (if present) by any suitable distance. In some examples, the longitudinal stripes 50 are spaced equidistant from each other. In other examples, the distance between adjacent longitudinal stripes 50 may vary.

Figure 5:
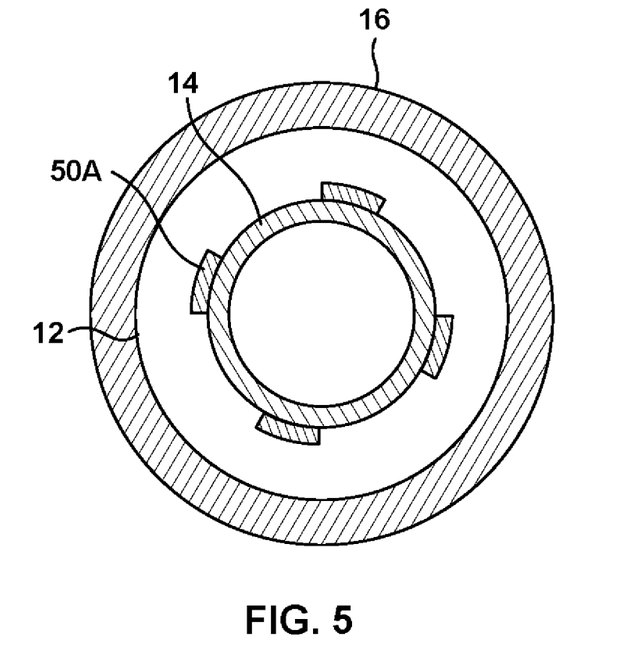
FIGS. 5 and 6 are example cross-sectional views of a catheter body, the guidewire tube of FIG. 4, and example longitudinal stripes of the coating.
Figure 6:
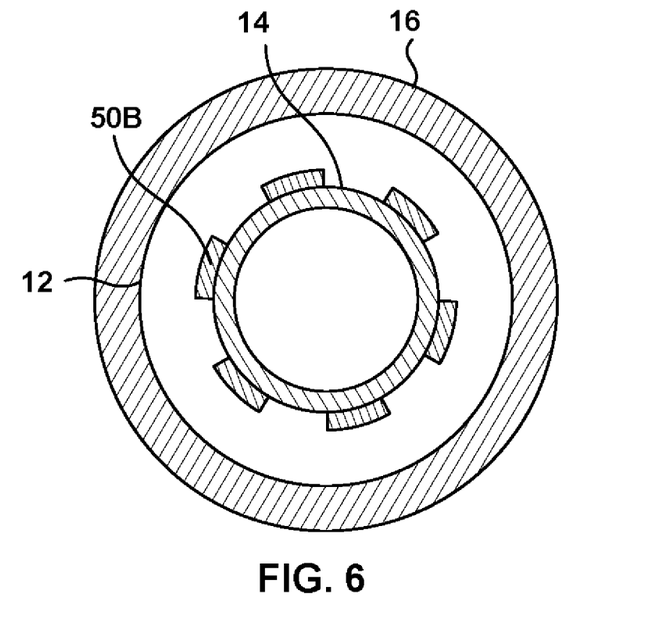

FIGS. 5 and 6 are example cross-sectional views of the catheter body 12, the guidewire tube 14, and example longitudinal stripes 50A and 50B of the coating 20. In the example shown in FIG. 5, the coating 20 is applied to define four longitudinal stripes 50A. In the example shown in FIG. 6, the coating 20 is applied to define six longitudinal stripes 50B. In other examples, the coating 20 can be applied to the guidewire tube outer surface 38 to define any suitable number of longitudinal stripes 50.

Figure 7:
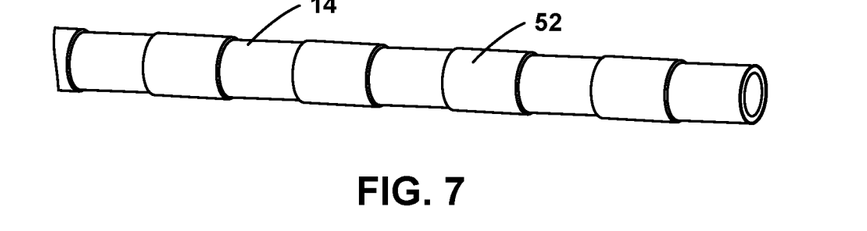
FIG. 7 is a perspective view of another example of a guidewire tube and a coating applied to an outer surface of the guidewire tube in lateral bands that are distributed along a longitudinal axis of the guidewire tube.

FIG. 7 is a perspective view of another example of the guidewire tube 14 and illustrates another example of a pattern with which the coating 20 can be applied to the guidewire tube outer surface 38. In the example shown in FIG. 7, the coating 20 is applied to define a plurality of lateral bands 52 that are each separated from an adjacent lateral band 52 along the longitudinal axis 11. That is, the lateral bands 52 are distributed longitudinally along the guidewire tube outer surface 38. In some examples, some or all of the lateral bands 52 each extends all the way around the outer perimeter of the guidewire tube 14 (in a direction orthogonal to the longitudinal axis 11) to define a closed ring. In other examples, some or all of the lateral bands 52 extend only partially around the outer perimeter of the guidewire tube 14 to define an open ring, e.g., a circumferential segment of coating 20.

In some examples, the lateral bands 52 have the same length (measured in a direction parallel to the longitudinal axis 11), while in other examples, at least two lateral bands 52 may have different lengths. The lateral bands 52 may have any suitable length, such as, but not limited to, about 0.5 cm to about 5 cm, about 1 cm to about 3 cm, or about 2 cm. In any of these examples, the lateral bands 52 can be spaced from an adjacent lateral band by any suitable distance, such as, but not limited to, about 0.5 cm to about 5 cm, about 1 cm to about 3 cm, or about 1 cm.

Figure 8:
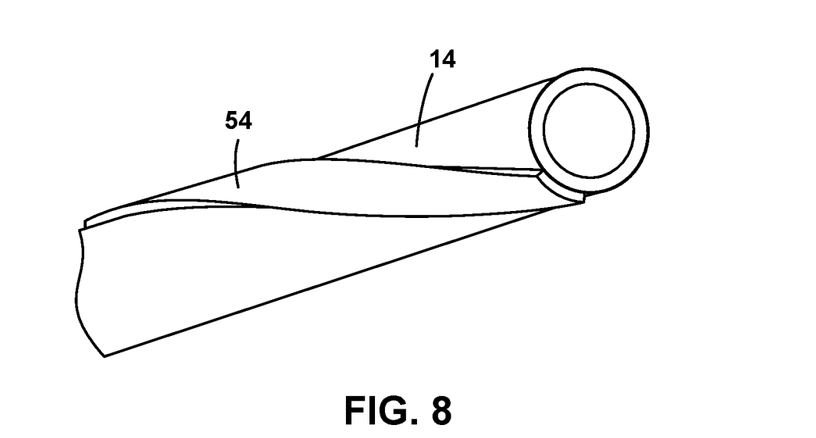
FIG. 8 is a perspective view of another example of a guidewire tube and a coating applied to an outer surface of the guidewire tube in a helical pattern.

FIG. 8 is a perspective view of another example of the guidewire tube 14 and illustrates another example of a pattern with which the coating 20 can be applied to the guidewire tube outer surface 38. In the example shown in FIG. 8, the coating 20 is applied to define a helix 54. The helix 54 extends around the guidewire tube outer surface 38, e.g., in a spiral configuration. In some examples, the helix 54 completes at least one full turn, such that it wraps around the entire outer perimeter of the guidewire tube 14. The helix 54 can have any suitable pitch, the pitch being a distance (measured along the longitudinal axis 11) between the adjacent turns of the helix 54. In some examples, the coating 20 is applied to the guidewire tube outer surface 38 to define multiple helixes 54 that extend around in the guidewire tube outer surface 38 in the same direction (e.g., parallel to each other) or are cross-wound (wound in opposite directions).

When the coating 20 is applied only partially over the guidewire tube outer surface 38, e.g., as described with reference to FIGS. 4-8, the percentage of the guidewire tube outer surface 38 that is covered by the coating 20 may be selected to enable the possibility of the coating 20, rather than the guidewire tube outer surface 38, contacting and engaging with the catheter body inner surface 36 when the catheter 10 is curved. For example, the longitudinal stripes 50 (FIG. 4) and the lateral bands 52 (FIG. 7) can be spaced relatively close to each other. As another example, the pitch of the one or more helices 54 (FIG. 8) or the spacing between multiple helices 54 (if present) can be selected to increase the surface area of guidewire tube outer surface 38 covered by the coating 20.

Figure 9:
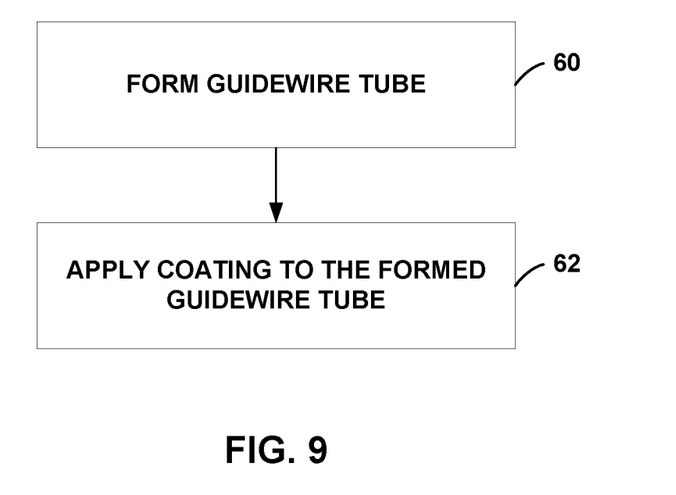
FIG. 9 is a flow diagram of an example method of forming a guidewire tube of a catheter.

FIG. 9 is a flow diagram of an example method of forming a guidewire tube of a catheter. FIG. 9 is described with reference to the catheter 10 and the guidewire tube 14 of FIGS. 1A and 1B, but in other examples, the method of FIG. 9 can be used to form other guidewire tubes having an elastomeric coating.

As shown in FIG. 9, the guidewire tube 14 is formed (60). For example, forming the guidewire tube 14 can including extruding the guidewire tube 14 to form a monolayer tube or a multilayer tube. After the guidewire tube 14 is formed (60), the coating 20 is applied to the already formed guidewire tube 14 (62). The coating 20 may be applied using any suitable technique, such as, but not limited to, dip coating, spraying, or brushing the coating material over the guidewire tube outer surface 38. In some examples, the coating 20 is applied over the entire guidewire tube outer surface 38 from the proximal end 14A to the distal end 14B of the guidewire tube 14. Dip coating can include, for example, dipping at least the portion of the guidewire tube 14 that is to include the coating 20 in the coating material.

In other examples, the coating 20 is applied to only part of the guidewire tube outer surface 38, e.g., only along the portion of the guidewire tube 14 extending through the catheter body lumen 22 and not on the portion of the guidewire tube 14 extending distally past the distal end 12B of the catheter body 12. In these examples, the coating 20 may be applied to the guidewire tube outer surface 38 using any suitable technique that enables some portions of the guidewire tube outer surface 38 to be devoid of the coating 20. For example, prior to applying the coating to the guidewire tube outer surface 38 by dip coating, spray coating, brush coating, or any other suitable coating application technique (62), a person or a machine can apply a mask over the portions of the guidewire tube outer surface 38 that are intended to be devoid of the coating 20. As another example, in some examples in which the coating 20 is applied by spray coating, a person or control circuitry of manufacturing equipment can be configured to start and stop the sprayer to apply the coating 20 to specific portions of the guidewire tube outer surface 38, e.g., to define the desired pattern of the coating 20. In some examples in which the coating 20 is applied by brush coating, a person or control circuitry of manufacturing equipment can control the brush to apply the coating 20 to specific portions of the guidewire tube outer surface 38, e.g., to define the desired pattern of the coating 20

Any of the example coating patterns described herein or other coating patterns can be used in combination with each other and/or in combination with applying the coating 20 to the guidewire tube outer surface 38 in particular longitudinal sections of the guidewire tube 14. For example, in some examples, the coating 20 may be applied to the guidewire tube outer surface 38 to define both longitudinal stripes 50 and lateral bands 52, which can overlap with each other or may be applied to different longitudinal sections of the guidewire tube 14. In examples, in which the coating 20 is present on one or more first longitudinal sections of the guidewire tube 14 but absent from one or more second longitudinal sections of the guidewire tube 14, e.g., the longitudinal section aligned with the balloon 16, the coating 20 may be applied to the one or more first sections of the guidewire tube outer surface 38 in a particular pattern or over the entire guidewire tube outer surface 38.

After the coating is applied to the already formed guidewire tube 14, the coating can be cured and/or dried.

The present disclosure includes the following examples.

In a first example, a catheter comprises a catheter body comprising a catheter body inner surface defining a lumen; a guidewire tube extending through the lumen and distally past a distal end of the catheter body; and an elastomeric coating applied to an outer surface of at least a portion of the guidewire tube extending through the lumen.

In a second example, the elastomeric coating of the catheter of the first example is configured to increase friction between the outer surface of the at least the portion of the guidewire tube and the catheter body inner surface.

In a third example, the elastomeric coating of the catheter of the first or second examples comprises a polymer having a hardness of 20 Shore A or less.

In a fourth example, the elastomeric coating of the catheter of any of the first through third examples is configured to stick to the catheter body inner surface.

In a fifth example, the elastomeric coating of the catheter of any of the first through fourth examples is dip coated, spray coated, or brushed over the outer surface of the at least the portion of the guidewire tube.

In a sixth example, the elastomeric coating of the catheter of any of the first through fifth examples is on the outer surface of an entire length of the guidewire tube.

In a seventh example, the elastomeric coating of the catheter of any of the first through fifth examples is on only a part of the outer surface of the guidewire tube.

In an eighth example, the elastomeric coating of the seventh example defines one or more longitudinal stripes.

In a ninth example, the elastomeric coating of the catheter of the seventh or eighth examples defines a plurality of lateral bands distributed along a length of the at least the portion of the guidewire tube.

In a tenth example, the elastomeric coating of the catheter of any of the seventh through ninth examples defines a helical pattern along a length of the at least the portion of the guidewire tube.

In an eleventh example, the catheter of any of the first through tenth examples further comprises a balloon connected to the guidewire tube, wherein the portion of the guidewire tube comprises a first portion, and wherein a second portion of the guidewire tube longitudinally aligned with the balloon is devoid of the elastomeric coating.

In a twelfth example, the guidewire tube of the catheter of any of the first through eleventh examples is a monolayer tube, the elastomeric coating being on an outermost surface of the monolayer tube.

In a thirteenth example, the guidewire tube of the catheter of any of the first through eleventh examples comprises a multilayer tube, the elastomeric coating being on an outermost surface of the multilayer tube.

In a fourteenth example, the catheter of any of the first through tenth examples further comprises a balloon connected to the guidewire tube.

In a fifteenth example, the proximal and distal ends of the balloon of the catheter of the fourteenth example are connected to the guidewire tube.

In a sixteenth example, a balloon proximal end of the balloon of the catheter of the fourteenth example is attached to the catheter body and a balloon distal end of the balloon is attached to the guidewire tube.

In a seventeenth example, a catheter comprise a catheter body defining a lumen; a guidewire tube extending through the lumen; and a polymer coating on an outer surface of at least a portion of the guidewire tube extending through the lumen, wherein the polymer coating is applied in a predetermined pattern and is configured to increase friction between the outer surface of the at least the portion of the guidewire tube and an inner surface of the catheter body.

In an eighteenth example, the polymer coating of the catheter of the seventeenth example comprises a polymer having a hardness of 20 Shore A or less.

In a nineteenth example, the polymer coating of the catheter of the seventeenth or the eighteenth examples is configured to stick to the catheter body inner surface.

In a twentieth example, the polymer coating of the catheter of any of the seventeenth through nineteenth examples is dip coated, spray coated, or brushed over the outer surface of the at least the portion of the guidewire tube.

In a twenty-first example, the predetermined pattern of the catheter of any of the seventeenth through twentieth examples extends along an entire length of the guidewire tube.

In a twenty-second example, the polymer coating of the catheter of any of the seventeenth through twentieth examples extends along only part of an entire length of the guidewire tube.

In a twenty-third example, the predetermined pattern of the catheter of any of the seventeenth through twenty-second examples comprises one or more longitudinal stripes.

In a twenty-fourth example, the predetermined pattern of the catheter of any of the seventeenth through twenty-third examples comprises a plurality of lateral bands distributed along a length of the at least the portion of the guidewire tube.

In a twenty-fifth example, the predetermined pattern of the catheter of any of the seventeenth through twenty-fourth examples comprises a helical pattern along a length of the at least the portion of the guidewire tube.

In a twenty-sixth example, the catheter of any of the seventeenth through twenty-fifth examples further comprises a balloon connected to the guidewire tube, wherein the portion of the guidewire tube comprises a first portion, and wherein a second portion of the guidewire tube longitudinally aligned with the balloon is devoid of the polymer coating.

In a twenty-seventh example, the guidewire tube of the catheter of any of the seventeenth through twenty-sixth examples is a monolayer tube, the polymer coating being on an outermost surface of the monolayer tube.

In a twenty-eighth example, the guidewire tube of the catheter of any of the seventeenth through twenty-sixth examples comprises a multilayer tube, the polymer coating being on an outermost surface of the multilayer tube.

In a twenty-ninth example, the catheter of any of the seventeenth through twenty-eighth examples further comprises a balloon connected to the guidewire tube.

In a thirtieth example, proximal and distal ends of the balloon of the catheter of the twenty-ninth example are connected to the guidewire tube.

In a thirty-first example, a balloon proximal end of the balloon of the catheter of the twenty-ninth example is attached to the catheter body and a balloon distal end of the balloon is attached to the guidewire tube.

In a thirty-second example, a method comprises forming a guidewire tube; applying an elastomeric coating to an outer surface of at least a portion of the guidewire tube; and positioning the portion of the guidewire tube in a lumen defined by an inner surface of a catheter body.

In a thirty-third example, the elastomeric coating of the thirty-second example is configured to increase friction between the outer surface of the at least the portion of the guidewire tube and the catheter body inner surface.

In a thirty-fourth example, applying the elastomeric coating to the outer surface of at least the portion of the guidewire tube in the method of the thirty-second or thirty-third examples comprises dipping at least the portion of the guidewire tube in the elastomeric coating.

In a thirty-fifth example, applying the elastomeric coating to the outer surface of at least the portion of the guidewire tube in the method of any of the thirty-second through thirty-fourth examples comprises spraying the elastomeric coating over the outer surface of at least the portion of the guidewire tube.

In a thirty-sixth example, applying the elastomeric coating to the outer surface of at least the portion of the guidewire tube in the method of any of the thirty-second through thirty-fifth examples comprises brushing the elastomeric coating over the outer surface of at least the portion of the guidewire tube.

In a thirty-seventh example, forming the guidewire tube in the method of any of the thirty-second through thirty-fifth examples comprises extruding the guidewire tube.

In a thirty-eighth example, a method comprises forming a guidewire tube; applying a polymer coating to an outer surface of at least a portion of the guidewire tube; and positioning the portion of the guidewire tube in a lumen defined by an inner surface of a catheter body, wherein the polymer coating is applied in a predetermined pattern and is configured to increase friction between the outer surface of the at least the portion of the guidewire tube and an inner surface of the catheter body.

In a thirty-ninth example, applying the polymer coating to the outer surface of at least the portion of the guidewire tube in the method of the thirty-eighth example comprises dipping at least the portion of the guidewire tube in the polymer coating.

In a fortieth example, applying the polymer coating to the outer surface of at least the portion of the guidewire tube in the method of the thirty-eighth or thirty-ninth examples comprises spraying the polymer coating over the outer surface of at least the portion of the guidewire tube.

In a forty-first example, applying the polymer coating to the outer surface of at least the portion of the guidewire tube in the method of any of the thirty-eighth through fortieth examples comprises brushing the polymer coating over the outer surface of at least the portion of the guidewire tube.

In a forty-second example, forming the guidewire tube in the method of any of the thirty-eighth through forty-first examples comprises extruding the guidewire tube.

Various examples have been described. These and other examples are within the scope of the following claims.

What is claimed is:

1. A catheter comprising:
   a catheter body comprising a catheter body inner surface defining a lumen;
   a guidewire tube extending through the lumen and distally past a distal end of the catheter body, wherein the distal end of the catheter body is fixed between proximal and distal ends of the guidewire tube; and
   an elastomeric coating applied to an outer surface of at least a portion of the guidewire tube extending through the lumen, wherein the elastomeric coating is configured to stick to the catheter body inner surface.

2. The catheter of claim 1, wherein the elastomeric coating is configured to increase friction between the outer surface of the at least the portion of the guidewire tube and the catheter body inner surface.

3. The catheter of claim 1, wherein the elastomeric coating comprises a polymer having a hardness of 20 Shore A or less.

4. The catheter of claim 1, wherein the elastomeric coating is dip coated, spray coated, or brushed over the outer surface of the at least the portion of the guidewire tube.

5. The catheter of claim 1, wherein the elastomeric coating is on the outer surface of an entire length of the guidewire tube.

6. The catheter of claim 1, wherein the elastomeric coating is on only a part of the outer surface of the guidewire tube.

7. The catheter of claim 6, wherein the elastomeric coating defines one or more longitudinal stripes.

8. The catheter of claim 6, wherein the elastomeric coating defines a plurality of lateral bands distributed along a length of the at least the portion of the guidewire tube.

9. The catheter of claim 1, further comprising a balloon connected to the guidewire tube, wherein the portion of the guidewire tube comprises a first portion, and wherein a second portion of the guidewire tube longitudinally aligned with the balloon is devoid of the elastomeric coating.

10. The catheter of claim 1, wherein the guidewire tube is a monolayer tube, the elastomeric coating being on an outermost surface of the monolayer tube.

11. The catheter of claim 1, wherein the guidewire tube comprises a multilayer tube, the elastomeric coating being on an outermost surface of the multilayer tube.

12. The catheter of claim 1, further comprising a balloon connected to the guidewire tube.

13. The catheter of claim 1, further comprising an expandable balloon, wherein a proximal end of the balloon is attached to the catheter body and a distal end of the balloon is attached to the guidewire tube.

14. The catheter of claim 1, wherein the guidewire tube comprises high-density polyethylene (HDPE).

15. A catheter comprising:
    a catheter body comprising a catheter body inner surface defining a lumen;
    a guidewire tube extending through the lumen and distally past a distal end of the catheter body, wherein the distal end of the catheter body is fixed between proximal and distal ends of the guidewire tube; and
    an elastomeric coating applied to an outer surface of at least a portion of the guidewire tube extending through the lumen, wherein the elastomeric coating is on only a part of the outer surface of the guidewire tube, and wherein the elastomeric coating defines a helical pattern along a length of the at least the portion of the guidewire tube.

16. A catheter comprising:
    a catheter body defining a lumen;
    a guidewire tube extending through the lumen, wherein a distal end of the catheter body is fixed between proximal and distal ends of the guidewire tube; and
    a polymer coating on an outer surface of at least a portion of the guidewire tube extending through the lumen, wherein the polymer coating is applied in a predetermined pattern and is configured to increase friction between the outer surface of the at least the portion of the guidewire tube and an inner surface of the catheter body, wherein the predetermined pattern comprises a helical pattern along a length of the at least the portion of the guidewire tube.

17. The catheter of claim 16, wherein the predetermined pattern comprises one or more longitudinal stripes.

18. The catheter of claim 16, wherein the predetermined pattern comprises a plurality of lateral bands distributed along a length of the at least the portion of the guidewire tube.

19. The catheter of claim 16, further comprising a balloon connected to the guidewire tube, wherein the portion of the guidewire tube comprises a first portion, and wherein a second portion of the guidewire tube longitudinally aligned with the balloon is devoid of the polymer coating.

20. The catheter of claim 16, further comprising an expandable balloon, wherein a proximal end of the balloon is attached to the catheter body and a distal end of the balloon is attached to the guidewire tube.

21. A catheter comprising:
    a catheter body comprising a catheter body inner surface defining a lumen;
    a guidewire tube extending through the lumen and distally past a distal end of the catheter body, wherein the distal end of the catheter body is fixed between proximal and distal ends of the guidewire tube; and
    an elastomeric coating applied to an outer surface of at least a portion of the guidewire tube extending through the lumen, wherein the elastomeric coating comprises a polymer having a hardness of 20 Shore A or less.

22. A method comprising:
    forming a guidewire tube;
    applying an elastomeric coating to an outer surface of at least a portion of the guidewire tube;
    positioning the at least the portion of the guidewire tube in a lumen defined by an inner surface of a catheter body, wherein positioning the at least the portion of the guidewire tube in the lumen comprises positioning the guidewire tube to extend through the lumen and distally past a distal end of the catheter body, and wherein the elastomeric coating is configured to stick to the inner surface of the catheter body; and fixing the distal end of the catheter body between proximal and distal ends of the guidewire tube.

23. The method of claim 22, wherein the elastomeric coating is configured to increase friction between the outer surface of the at least the portion of the guidewire tube and the catheter body inner surface.

24. The method of claim 22, wherein applying the elastomeric coating to the outer surface of the at least the portion of the guidewire tube comprises dipping the at least the portion of the guidewire tube in the elastomeric coating.

25. The method of claim 22, wherein applying the elastomeric coating to the outer surface of the at least the portion of the guidewire tube comprises spraying the elastomeric coating over the outer surface of the at least the portion of the guidewire tube.

26. The method of claim 22, wherein applying the elastomeric coating to the outer surface of the at least the portion of the guidewire tube comprises brushing the elastomeric coating over the outer surface of the at least the portion of the guidewire tube.

27. The method of claim 22, wherein applying the elastomeric coating to the outer surface of the at least the portion of the guidewire tube comprises applying the elastomeric coating to the outer surface of the at least the portion of the guidewire tube in a predetermined pattern.

\* \* \* \* \*